United States Patent [19]

Castanho, Jr.

[11] 4,410,246

[45] Oct. 18, 1983

[54] SYSTEM AND MECHANISM OF FEEDING, TRACTION, SHUTTERING AND FILM ADJUSTMENT IN PROGRAMMABLE AUDIOVISUAL APPARATUS, WITH RAPID FRAME CHANGE

[76] Inventor: Elio D. Castanho, Jr., 510 Ademar de Barros Ave., Sao Jose dos Campos, Sao Paulo, Brazil

[21] Appl. No.: 293,955

[22] Filed: Aug. 18, 1981

[30] Foreign Application Priority Data

Aug. 20, 1980 [BR] Brazil .................................. 8005253

[51] Int. Cl.$^3$ ............................................. G03B 21/38
[52] U.S. Cl. ...................................... 352/169; 352/17; 352/128; 352/162; 352/163
[58] Field of Search ................. 352/17, 126, 128, 162, 352/164, 227, 169, 121, 137

[56] References Cited

U.S. PATENT DOCUMENTS

| 1,298,600 | 3/1919 | Taylor | 352/162 |
|---|---|---|---|
| 1,417,807 | 5/1922 | Delume | 352/164 |
| 1,727,900 | 9/1929 | Patterson | 352/227 |
| 1,900,925 | 3/1933 | Frappier et al. | 352/227 |
| 2,426,838 | 9/1947 | Miller | 352/128 |
| 2,503,083 | 4/1950 | Waller | 352/17 |
| 2,575,203 | 11/1951 | Wolfner | 352/17 |
| 2,606,476 | 8/1952 | Waller et al. | 352/17 |
| 3,692,390 | 9/1972 | Siegel | 352/17 |
| 3,790,261 | 2/1974 | Threlkelo | 352/128 |
| 3,844,643 | 10/1974 | Aoki | 352/17 |
| 4,004,746 | 1/1977 | Aruanno | 352/128 |

FOREIGN PATENT DOCUMENTS 754315 11/1933 France .............................. 352/164

OTHER PUBLICATIONS

Alien Property Custodian Publication Ser. No. 316,983 5-4-43, Fries.

Primary Examiner—Monroe H. Hayes
Attorney, Agent, or Firm—Steinberg & Raskin

[57] ABSTRACT

The invention relates to a system and mechanism of film feeding, traction, shuttering and adjustment in programmable audiovisual apparatus, with rapid frame change, which executes the indexing of one frame to the next one in accordance with a pre-established programmed signal, indexing only one frame at each signal, characterized by apparatus which renders the time taken to effect the frame change imperceptible and also allowing the establishing of all the stages of projection of animation, varying from one static frame at a time, up to the particular frame change speed desired.

6 Claims, 8 Drawing Figures

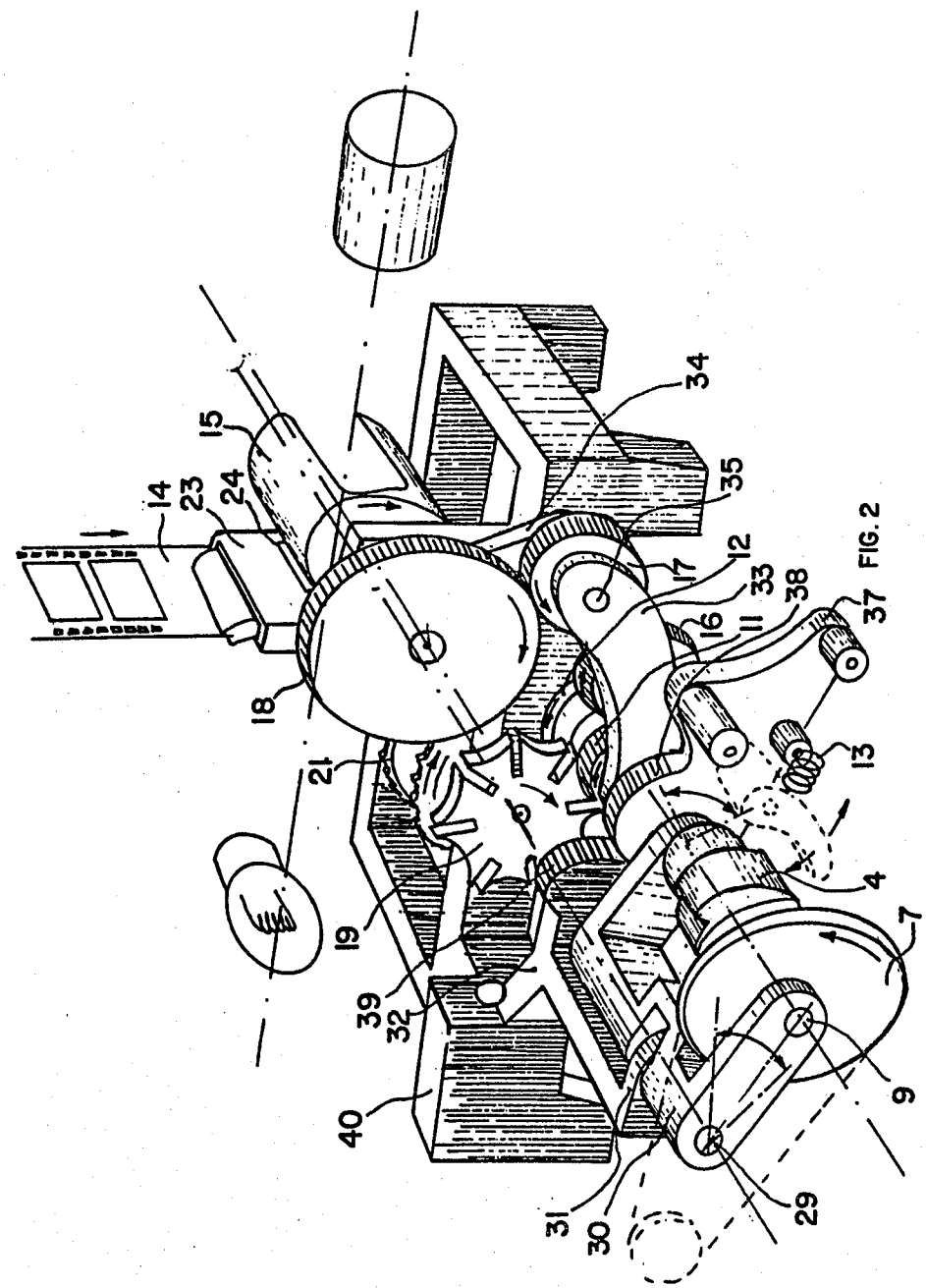

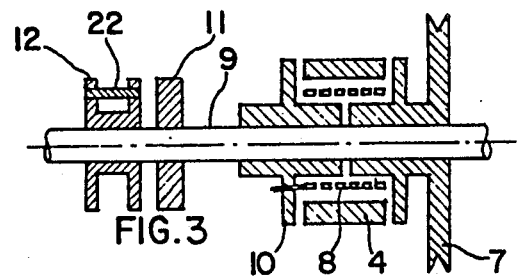
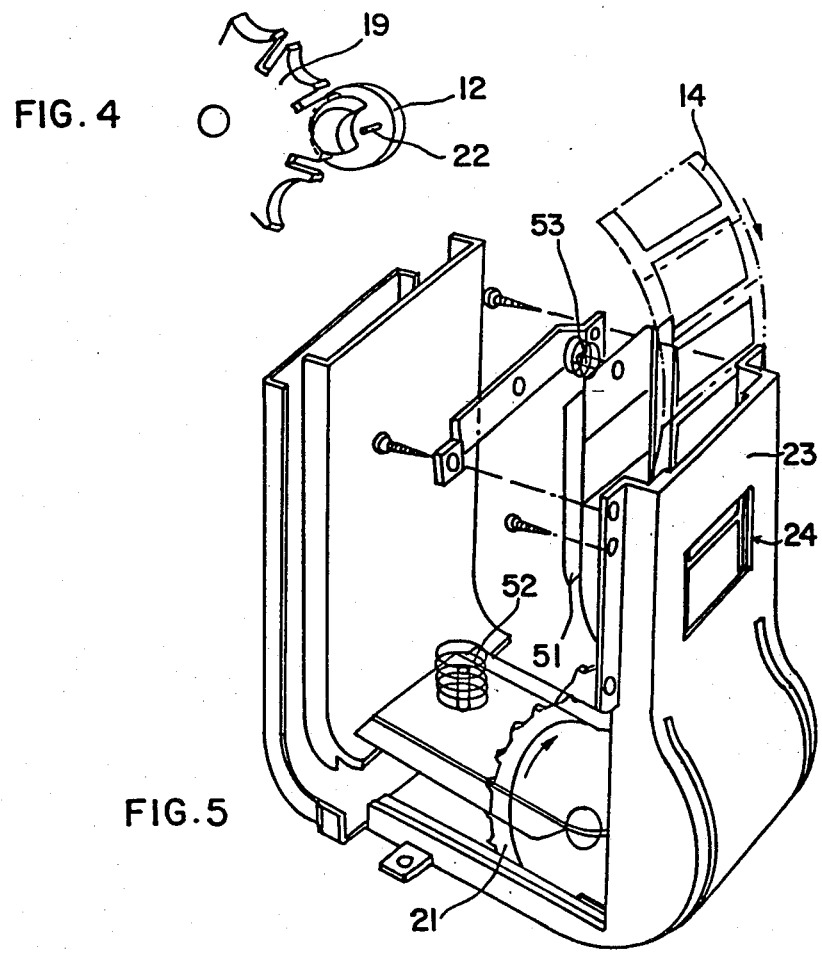

SYSTEM AND MECHANISM OF FEEDING, TRACTION, SHUTTERING AND FILM ADJUSTMENT IN PROGRAMMABLE AUDIOVISUAL APPARATUS, WITH RAPID FRAME CHANGE

BACKGROUND OF THE INVENTION

The present invention relates to a system and mechanism for the presentation of audiovisuals applied to the field of information.

The mechanical-electronic audiovisual systems of today consist of cine (moving) and fixed image projectors, the latter being known as "slide projectors" or "film strip" projectors.

In the case of cine, the projection is accomplished by the sequential exposure of the image, frame by frame, presented in a fixed frequency such that the photographic sequence projects images of the same object, adopting however, progressively altering positions. Nevertheless, the sound corresponding to the projected scene is read on a band of the film strip by means of optic or magnetic recording. Consequently, it is necessary to keep the film strip moving, changing static images in order to develop and continue the sound track. This being the case, according to established international standards, 18 or 24 frames per second are consumed, but always with a fixed frequency for reasons inherent in the technique of synchronization of sound and image, demanding therefore, great quantities of film even when projecting a fixed image.

In the case of slide or film strip projectors the projection is accomplished by projecting, also frame by frame, static images, when the frames are changed by a system of levers so that each change of frame is pursuant to a command read on a magnetic or independently perforated tape which is recorded, transcribed on the tape on a track at the side of the corresponding sound.

The projection of the image together with the sound begins with a slide projector coupled to a tape player (external or integrated in the projector) permitting, as can be seen, greatly reduced production costs as compared to cine-sound productions resulting therefore in more intensive use and easier access to the the market. Consequently, the ideal would be the possibility of movement in some scenes at times essential for clarifying the object of the projection and that this movement, or in other words this progressive change of frames were capable of having its frequency programmed in time with the audiovisual. Hence, an audiovisual which is to have such movement should have greater frame storage. Currently developed audiovisual systems handle carousels or magazines of up to 140 frames in the case of slides, which for reasons of movement demand spacious storage area, and up to 72 frames in the case of film strip.

The time intervals between frame changes obtained by these projectors are limited by the mechanical design to one frame every 2 seconds or one frame per second using special external equipment. In order that the audience does not see the frames moving while they are being changed, projection is terminated leaving the screen dark for a period of time of about 2 seconds in the former case and about 1 second in the latter, causing the iris of the eyes to dilate during the change and contract during the projection.

SUMMARY OF THE INVENTION

With the above in view, the invention mainly comprises a system and mechanism for feeding traction, shuttering, and adjustment of film in programmable audiovisual apparatus with rapid frame change, the projection of which obeys command signals previously established and recorded together with the sound, which produce changes of frame with a shuttering time reduced to such a degree as to be imperceptible to the human eye. The present invention responds to the frame change interval which is established and in this way projects static images or sequential images giving the idea of movement identical with that of cine film. To make this possible the mechanism provides for, besides a sufficiently rapid frame change, the requisite synchronised closure of the shutter at the instant of indexing from one frame to the next. Taking into account that which has been said so far about the state of the art, the capacity of slide storage should be increased several times so as to be able to make use of a number of frames sufficient to show animated sequences in an ordinary audiovisual.

Thus, the present invention, besides other advantages, offers a rapid change of slides and eliminates the need for the use of two separate projectors which permit both projection of individual frames as well as animation.

Although the change from one frame to the next is extremely rapid such that it is not possible to detect the change itself nor the time taken to close the projection shutter during this change, the present invention makes this change only on command and changes only one frame per command signal, thus making it possible to establish whatever change interval may be desired making the movement of images independent of the sequence of projection and only dependent on sound, i.e., exactly the opposite of cine film where sound is the slave of the projection sequence.

The power necessary for the change from one frame to another becomes considerably reduced by the miniaturization of the shutter system and by the system of film guides which accommodate the frames during their passage and position the film in the projection aperture eliminating the otherwise necessary film tensioning reducing friction in the change. Each change is made in about 20 milliseconds to accomodate the needs of the retention of the retina and would need a motor 50 times more powerful than that used in a slide or film strip projector, increasing the weight and volume of the motor as well as the system as a whole.

The present invention presents, as an additional advantage, greater reduction in weight in comparison with conventional systems, in this way making a greater number of applications and audiovisual means possible.

The storage capacity of the loop forming a part of the feeding and storage aspect of the invention is hundreds of slides. Although comprising hundreds of slides, the system in question permits, e.g., in a 10 cm diameter roll inside the equipment, more than 23 slide carousels, signifying a volume up to 30 times smaller than conventional systems, may be stored. These frames may be stored, ready for projection, in a closed circuit loop in such a way that having projected the last slide, the system is again ready to restart the projection at the beginning of the first program, making the application easier in situations where it is necessary to continually project the same programs.

This film loop functions thanks to the rotation of the film support disc and the output guide system of the film reel.

The synchronization system of the shutter is provided with a compensation mechanism to allow complete projection of the frame in whatever position the film happens to be even during the readjustment of the position of the film shutter traction system.

DESCRIPTION OF THE DRAWINGS

The invention is further illustrated in connection with the accompanying drawings, in which

FIG. 2 is a general perspective of the quick-change frame mechanism, illustrating the angular movement of the clutch support about a pivot, said movement causing the multiplication of the angular movement of the spline support;

FIG. 3 is a section illustrating the clutch assembly as well as the gear and half-moon shaped component (hereafter referred to simply as the HM component);

FIG. 4 is a detail in perspective, of the pulley mechanism;

FIG. 5 is a detail in perspective of the guides emphasizing the path of the film therethrough and showing the mechanical adjustment of the position of the film by means of the sprocket and the film handling system;

DESCRIPTION OF PREFERRED EMBODIMENTS

Figure 1:
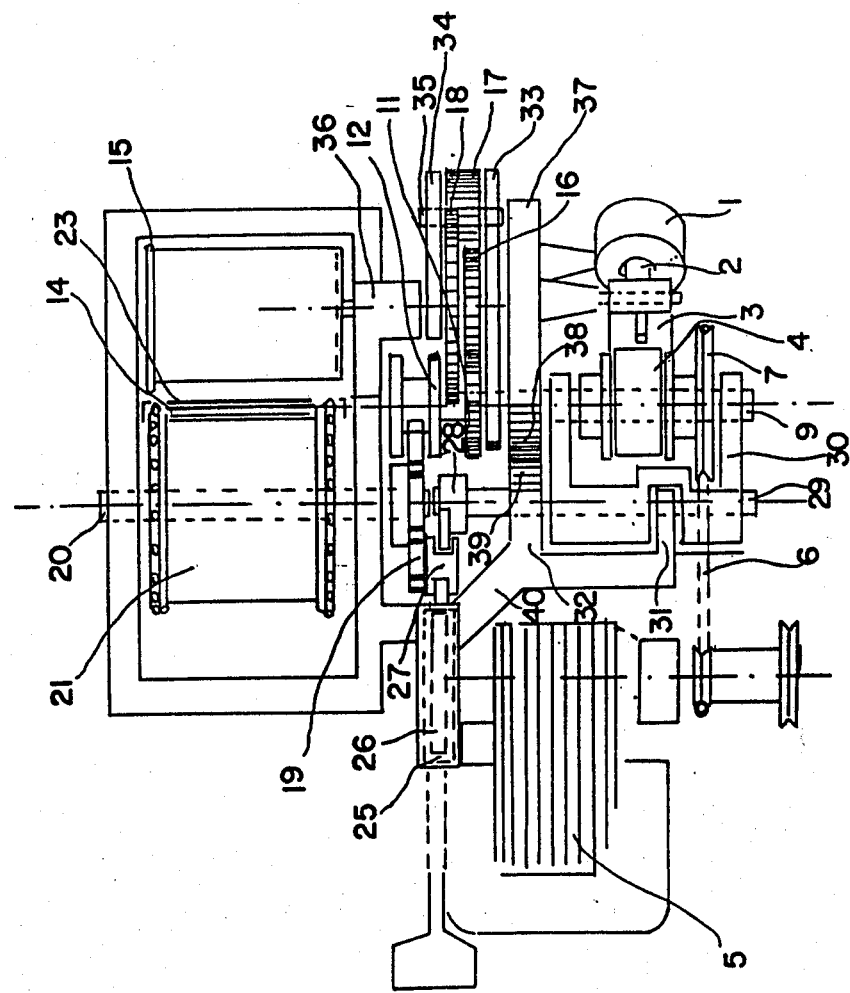
FIG. 1 is a general plan view of the quick-change frame mechanism.

The mechanical traction system which indexes the film frame one frame to the subsequent one functions in response to a command associated with the sound equipment associated with the system. The mechanism receives the command in the form of an electrical pulse delivered to a solenoid 1 which retracts the core 2 thereby retracting the spline 3 thereby freeing the ratchet 4.

The motor 5 runs continuously and transmits by means of a belt 6, rotation to the pulley wheel 7 which turns freely round the shaft 9. As can be seen in FIG. 3, the ratchet 4, when freed, permits the closing of the spring 8 which engages the pulley wheel 7. As can be seen in FIG. 3, the spring 8 has one end mountd on the clutch plate 10 and the other end mounted on the ratchet 4. When the spring 8 engages the pulley wheel 7 it receives and transmits the rotation of the pulley wheel 7 which in turn drives the clutch wheel 10 which transmits the rotation to shaft 9 on which it is mounted.

The gear 11 and the HM component 12 are also fixedly mounted on the shaft 9 and rotates therewith. The solenoid spring 13 returns the spline 3 against the ratchet 4 opening the spring 8 thus stopping the rotation of the entire assembly formed by the ratchet 4, spring 8, shaft 9, clutch plate 10, gear 11, and HM component 12, the drive wheel 7 continuing to freely rotate round the shaft 9. At this time there occurs a twofold activity; with each complete rotation, i.e., after freeing the spline 3 from the ratchet 4, the film frame is changed and the film 14 advanced to the next frame while at the same time the shutter 15 is rotated. The gear 11 rotates the shutter 15 by means of the rotation transmitted by the primary gear 16, the secondary gear 17, and the reduction gear 18. The HM component 12 and the rotor 19 form a pulley mechanism as in FIG. 4 which draws the film 14 across the sprocket shaft 20 and sprocket 21. The HM component 12 only initiates the frame change by means of the sprocket 21 after the shutter 15 has rotated sufficiently to optically block the projection to prevent the changing frames from being projected during the change period. The sprocket 21 and the sprocket shaft 20 and the rotor 19 rotates jointly in such a way that the sprocket 21 draws the film 14 only when the pin 22 is once again free from a slot of the rotor 19 thus leaving the sprocket 21 and the film 14 locked for projection. The HM component 12 continues to rotate until the pin completes a 360° revolution jointly with the gear 11, primary gear 16, secondary gear 17, and reduction gear 18, leaving the shutter 15 in a completely open position optically unblocking the projection.

In accordance with what was stated before, FIG. 5 shows the film 14 with a frame in projection not exactly coinciding with the aperture 24 of the guide 23. By the fact that the perforation on the film strip 14 is secured by the sprocket teeth, it is enough to turn the sprocket 21 until the frame coincides with the aperture 24. As can be observed in FIG. 1, this is done by manually turning the external spindle 25 in an appropriate direction, which causes an internal spindle 26 threadedly cooperating with external spindle 25 to push or pull the anterior rod 27 or posterior rod 28; the posterior rod 28 is mounted on the pivot 29 which is itself mounted on the gear support 31 and on the toothed support 32 of chassis 40, allowing the HM component 12 together with the shaft 9, in an angular movement concentric to the pivot 29, to produce a circular movement in the rotor 19 and consequently on the sprocket 21 so as to draw the film 14 within the guide 23 until the frame is made to coincide with the aperture 24.

This procedure, called aperture adjustment, passes the transmission rotation to the shutter 15 via the gear 11, primary gear 16, secondary gear 17, and reduction gear 18, the shafts of which are fixed to the lower arm 33 and upper arm 34 which move themselves in concert one with the other by the secondary shaft 35 and articulated in the appendix 36 and shaft 9, maintaining the gearing.

Nevertheless, the adjustment of the frame to the aperture would normally transmit a rotation to the shutter partially blocking the projection. This rotation however is neutralized at its point of origin by the support of the spline the base of which is a fixed semi-gear centered with a shaft and coupled to the toothed support of the chassis centered with a pivot so that when the aperture is adjusted, revolving the assembly formed by the external spindle, internal spindle, anterior rod, posterior rod, pivot, the gear support and the shaft it obliges the spline support with its fixed semi-gear coupled to the toothed support of the chasis, to increase the angle described by the spline support causing the spline to push the feed ratchet and the whole assembly formed by the spring, clutch plate, shaft, gear, primary gear, secondary gear, and reduction gear to which it is coupled, compensating for the shutter position so as to completely unblock the projection.

The mechanical system feeds the film in accordance with its frequency of frame change, variable with pre-established programmed pulses while rewinding the already projected film.

Figure 6:
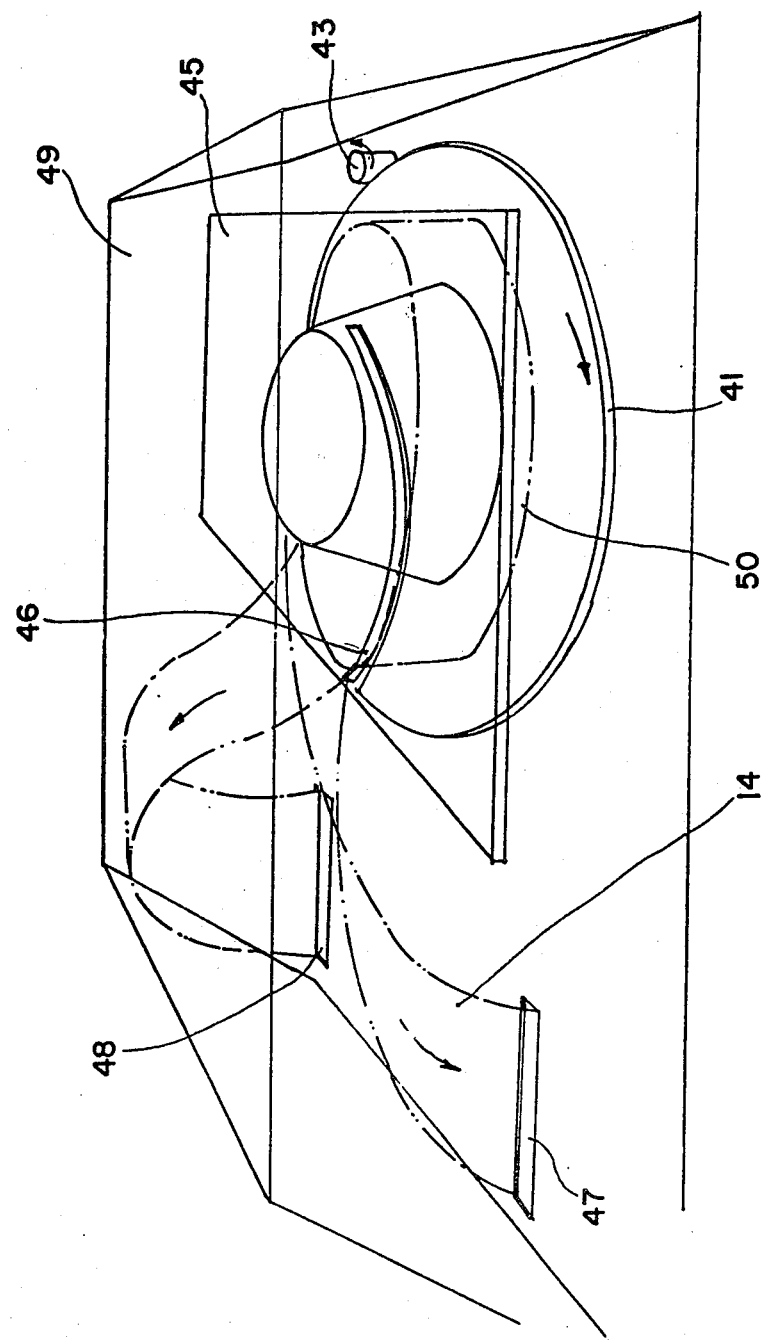
FIG. 6 is a general perspective of the film feed system illustrating its storage, entry and exit.
Figure 7:
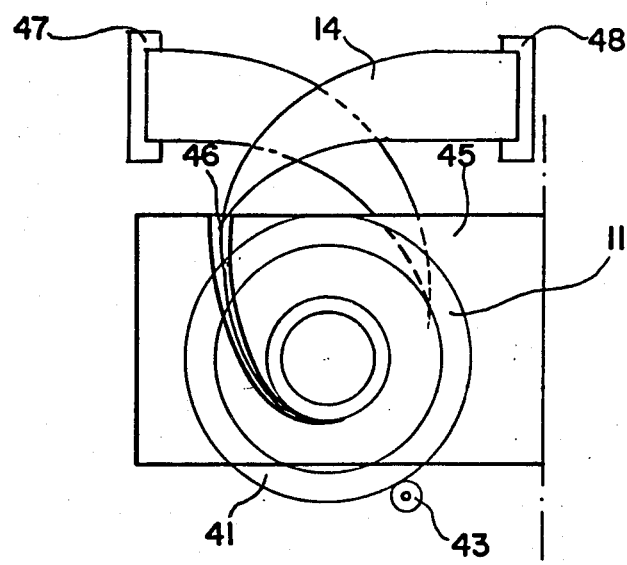
FIG. 7 is a plan view of the film feed system.
Figure 8:
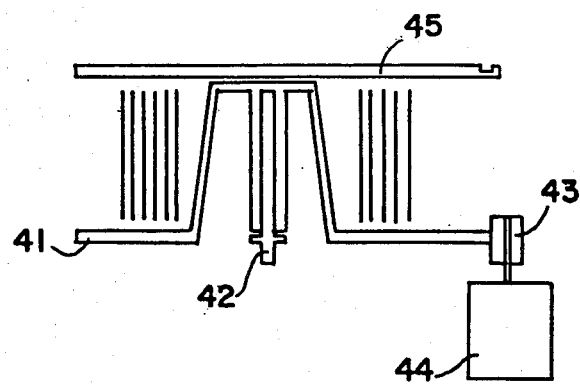
FIG. 8 is a vertical view in section of the film feed system.

As can be seen in FIG. 6, the film spool situated in its reel rests above a disc which revolves round the shaft actuated by the pulley of the motor. The film exits from its reel by the central part. In order that this exit be executed smoothly, the film is fed along a slot in a plate. The slot establishes the exit point of the film. The plate accommodates the film coming out of the mechanism after having been projected, during the rewinding.

The spooled film strip accepts various lengths and as its weight increases so too does the clutch effect which occurs because of the friction between the spooled film 14 and the disc 41.

The spooling action generated by the friction between the spooled length of film 14 and the disc 41 is compensated by the film 14 coming out of the mechanism exit 47 which only permits the spooling of one frame each time that another frame is changed, and for this to happen, the inlet 48 of the mechanism will already have received one more frame, subtracting it from the spooled length of film 14.

Nevertheless, the film 14 after the slot 46 and before the mechanism inlet 48, is able to expand in excess which is compensated, limiting itself to the curvature of the outlet of the slot 46 by means of the top 49 causing this length of film 14 to be short and have enough tension to avoid excess feeding.

The disc 41 has a conical central part the geometry of which facilitates the output of the spooled length of film. The slot 46 begins in the central region of the spooled length of film 14 and gradually widens allowing the film to establish an ideal path between the spooled length, top 49 and the mechanism inlet.

The interconnection between the film traction system and the storage and feeding system is effected by the system of guides by which the film passes to the projection aperture 24 where the frame is projected. The system comprising the guide 23 permits the passage of the film 14 in its interior. The film is positioned in front of the aperture flat and extended enough to be projected, by means of the internal guide 51 tensioned by the lower spring 52 and upper spring 53 eliminating the necessity of applying tension to the film 14. The lower spring 52 and upper spring 53 alleviate the pressure of the internal guide 51 at each frame change, facilitating the passage of the film when required.

The present invention represents a great technological advance in the field of audiovisuals while at the same time being of simple construction and easy to maintain, making it possible to be easily produced for use with the conventional means available on the market.

Low cost allied to high efficiency makes it possible for the system, besides having other advantages as was said previously, to fill the existing gap between what is known as slide projectors and cine projectors, making the image become dependent upon the sound.

The fact that the present invention makes it possible to have the image dependent upon the sound causes the production costs of audiovisuals to be drastically reduced.

In summary the present invention comprises a mechanism which feeds and stores the film composed of a disc 41 over which a spooled length of film 14 is accommodated which is guided to an exit by the slot 46 of plate 45 which also guides the film 14 to be rewound. The disc 41 is driven by the motor 44 by means of a pulley 43. The film has its output controlled by a top 49 and is presented for projection by the entry 48 and returns by means of exit 47 to be rewound on the disc 41.

The system of the invention which drives, adjusts and operates the shutter comprises the solenoid 1 which receives the program pulse, retracts the core 2 which pulls the spline 3 to free the ratchet 4. When the motor 5 is turning, the belt 6 will drive the pulley wheel 7 which upon becoming free of ratchet 4 couples the spring 8 to the clutch plate 10 rotating the shaft 9.

The traction system cooperates with the rotating shaft 9 and includes the HM component 12 which turns the slotted rotor 19, the shaft 20 and the sprocket 21 thereby pulling the film 14.

Regarding the shuttering system, the same shaft 9 has a gear 11 mounted thereon which will turn the shutter 15 by means of the primary gear 16, a secondary gear 17 and a reduction gear 18.

Finally, with respect to the means for precisely adjusting the position of the frame with respect to the aperture, the external spindle 25 drives the clutch support 30 by means of the internal spindle 26, anterior rod 27, the posterior rod 28 and the pivot 29. The clutch support 30 in which the shaft 9 rotates provides angular movement to the sprocket 21, the teeth of which penetrate the perforations in the film 14 to draw the same into the interior of the guide 23 whereby adjustment of the frame with respect to the aperture 24 is accomplished by means of the HM component 12 coupled with the rotor 19.

What is claimed is:

1. Audiovisual apparatus including film having a plurality of successive film frames and shutter means having a shutter frame, said film and shutter frames being situatable along a common optical axis for projection, comprising:

a shaft mounted for rotation;

a pulley mounted on said shaft for free rotation with respect thereto, said pulley being adapted for continuous rotation on said shaft;

clutch means fixed to said shaft for rotation therewith;

selectively actuatable ratchet means for coupling said clutch means when actuated to said continuously rotating pulley to rotate said shaft through only a single revolution;

a solenoid coupled to said ratchet means for actuating the same upon receiving a pulse signal whereby said shaft rotates to a single revolution;

said shutter means being mounted for rotation with respect to an axis to move said shutter frame between a projecting position in which said shutter frame is optically aligned with said optical axis for projection of said single film frame and an obstructing position wherein the shutter frame is out of alignment with with the optical axis so as to optically block projection of a film frame;

shutter rotating means coupled to said shaft for rotating said shutter means from a projecting position through obstructing positions and then to a projecting position upon rotation of said shaft through a single revolution; and means for advancing said film coupled to said shaft by coupling means such that for each rotation of said shaft, said film is advanced a distance corresponding to a single film frame in a manner such that advancement of said film occurs only after said shutter means has obtained said obstructing position.

2. The combination of claim 1 wherein said shutter means is mounted on a rotatable shutter axle and wherein said shutter rotating means comprises a first gear mounted on said shaft, a reducing gear mounted on said shutter axle, and at least one intermediate gear meshing with said first and reducing gears.

3. The combination of claim 2 wherein said means for advancing said film comprises a sprocket mounted on a rotatable sprocket axle and wherein said coupling means comprises a component fixed to said shaft for rotation therewith, said component including a pin having an axis extending parallel to said shaft adapted to rotate therearound upon rotation of said shaft and a rotor fixed to said sprocket axle having a plurality of substantially radially extending slots formed therein, said rod adapted to enter into and retract from a respective one of said slots during a single revolution of said shaft to rotate said rotor and said sprocket axle an amount whereby said film advances to bring a next successive film frame into optical alignment with said optical axis.

4. The combination of claim 3 further including a film feeding mechanism comprising a disc adapted to be driven by a motor, the film in spool form being situated on said disc, a plate situated over said film spool, and a slot formed in said plate through which said film passes.

5. The combination of claim 4 further including a traction mechanism cooperating with said sprocket, said traction mechanism comprising a guide member in which said sprocket is situated, said guide member having a projection aperture formed therein, and an internal guide situated contiguously with said film aperture, said internal guide cooperating with upper and lower springs to position said film with respect to said aperture.

6. The combination of claim 5 further including a precision film-aperture adjustment mechanism including a chassis having a gear support in which a pivot supporting said clutch is mounted, external spindle means mounted on said chassis, an internal spindle threadedly situated within said external spindle means, an anterior rod mounted on said pivot and a posterior rod mounted on said pivot, said anterior and posterior rods cooperating with said internal spindle whereby selective actuation of said external spindle means causes respective movement of said pivot which in turn results in movement of said clutch and said shaft to provide a circular movement of said rotor and sprocket wheel to position the film within said guide to correlate with said aperture.

* * * * *